(12) United States Patent
Barakat et al.

(10) Patent No.: US 11,287,415 B2
(45) Date of Patent: Mar. 29, 2022

(54) URINE HOME ANALYSER

(71) Applicant: WITHINGS, Issy les Moulineaux (FR)

(72) Inventors: Christelle Barakat, Paris (FR); Nadine Buard, Meudon (FR); Eric Carreel, Meudon (FR); Cédric Hutchings, Sunnyvale, CA (US)

(73) Assignee: WITHINGS, Issy les Moulineaux (FR)

( * ) Notice: Subject to any disclaimer, the term of this patent is extended or adjusted under 35 U.S.C. 154(b) by 942 days.

(21) Appl. No.: 15/395,337

(22) Filed: Dec. 30, 2016

(65) Prior Publication Data

US 2018/0188231 A1    Jul. 5, 2018

(51) Int. Cl.
| | | |
|---|---|---|
| *G01N 33/493* | (2006.01) | |
| *G01N 27/414* | (2006.01) | |
| *G01N 27/27* | (2006.01) | |
| *G01N 27/416* | (2006.01) | |
| *G01N 33/84* | (2006.01) | |
| *G01N 33/487* | (2006.01) | |
| *C12Q 1/00* | (2006.01) | |
| *G01N 21/25* | (2006.01) | |
| *A61B 10/00* | (2006.01) | |

(52) U.S. Cl.
CPC ......... *G01N 33/493* (2013.01); *A61B 10/007* (2013.01); *C12Q 1/001* (2013.01); *G01N 21/25* (2013.01); *G01N 27/27* (2013.01); *G01N 27/414* (2013.01); *G01N 27/4163* (2013.01); *G01N 33/48792* (2013.01); *G01N 33/84* (2013.01)

(58) Field of Classification Search
None
See application file for complete search history.

(56) References Cited

U.S. PATENT DOCUMENTS

| | | | | |
|---|---|---|---|---|
| 4,436,610 A | * | 3/1984 | Enzer | G01N 33/49 204/400 |
| 4,961,431 A | * | 10/1990 | Ikenaga | A61B 5/14507 600/573 |
| 5,111,539 A | * | 5/1992 | Hiruta | A61B 5/02241 4/661 |

(Continued)

FOREIGN PATENT DOCUMENTS

JP     11311615 A  * 11/1999

OTHER PUBLICATIONS

JPH11311615 (A)—Machine Translation (Year: 1999).*

*Primary Examiner* — Sean P Dougherty
*Assistant Examiner* — Benjamin S Melhus
(74) *Attorney, Agent, or Firm* — von Briesen & Roper, s.c.

(57) ABSTRACT

A urine analyzer device, configured to be installed in a toilet bowl, to be used several times, the device comprising a holder member, to attach the device to the rim of the toilet bowl, an electronic unit, enclosed in a housing, a urine reception area, with at least one electro-chemical sensor, configured to measure a quantity of at least one substance contained in urine, such as physiological compound or chemical component, a wireless coupler to send resulting data to a remote computing device, wherein the electro-chemical sensor comprises at least a ion selective Field Effect Transistor (ISFET), configured to sense levels of one or more physiological ions, thereby providing a urine analyzer device, readily available at home, simply installed in a toilet bowl, and that can be used several times subsequently.

22 Claims, 5 Drawing Sheets

(56) References Cited

U.S. PATENT DOCUMENTS

| | | | | |
|---|---|---|---|---|
| 5,198,192 A * | 3/1993 | Saito | A61B 5/14532 | 4/314 |
| 5,720,054 A * | 2/1998 | Nakayama | G01N 33/493 | 4/420 |
| 6,021,339 A * | 2/2000 | Saito | G01N 33/48785 | 600/345 |
| 6,572,564 B2 * | 6/2003 | Ito | A61B 5/14507 | 600/573 |
| 7,148,070 B2 * | 12/2006 | Minter | A61B 10/007 | 436/169 |
| 9,595,185 B1 * | 3/2017 | Hall | G01G 23/3735 | |
| 2001/0031913 A1 * | 10/2001 | Ito | A61B 5/14507 | 600/300 |
| 2005/0261605 A1 * | 11/2005 | Shemer | G01N 21/31 | 600/573 |
| 2008/0105566 A1 * | 5/2008 | Kitawaki | G01N 21/03 | 205/775 |
| 2008/0265985 A1 * | 10/2008 | Toumazou | G01N 27/4148 | 327/566 |
| 2010/0301398 A1 * | 12/2010 | Rothberg | G01N 27/414 | 257/253 |
| 2011/0092786 A1 * | 4/2011 | Longoni | A61B 5/14507 | 600/345 |
| 2014/0348707 A1 * | 11/2014 | King Smith | H01L 21/02186 | 422/82.03 |
| 2015/0342575 A1 * | 12/2015 | Hall | E03D 9/00 | 600/573 |
| 2016/0000378 A1 * | 1/2016 | Hall | A61B 5/0075 | 702/19 |
| 2017/0022536 A1 * | 1/2017 | Velazquez | A61B 10/007 | |
| 2018/0184906 A1 * | 7/2018 | Prokopp | A61B 5/4343 | |

\* cited by examiner

URINE HOME ANALYSER

FIELD OF THE DISCLOSURE

The present invention relates to a urine analyser device, which can be used at home; the invention targets especially an autonomous urine analyser device which can be installed in the bowl of the toilet.

BACKGROUND OF THE DISCLOSURE

As known, urine is an important source of information that reflects the health condition of an individual. Several biological parameters are reflected in urine. Absolute levels of several biological parameters and also evolution over time of several biological parameters are interesting to be obtained from samples of urine. It is a goal to monitor various health parameters, otherwise called 'bio-markers', that can be deduced from periodic urine analysis at home in a non-medical environment. This is generally helpful to help enhance personal wellness and help reduce some risk factors.

Various minor disorders can be detected early by analysis of evolutions and trends of personal biological parameters.

Additionally, dysfunctions such as pancreatic disorders (typically, diabetes), hypohepatia, and kidney disorders, can be detected advantageously in a non-invasive manner by performing quantitative analysis of certain urine constituents, such as glucose, protein, urobilinogen, occult blood and other substances.

Accordingly, there have been proposed in the art toilets having a urine analysis function which are capable of performing sampling and analysis of urine so as to assist the individuals in rendering their health check by making use of toilets provided in at home, without excluding offices and other facilities.

It is known in the art, as taught by U.S. Pat. No. 5,720,054 [TOTO], to install a urine analyser device in the bowl of the toilet. However, the known devices are very complicated, requires many connections, and are expensive and furthermore it does not handle multiple users.

Therefore, there is a need to bring new solutions to provide urine analyser devices to be used at home in the standard toilet.

SUMMARY OF THE DISCLOSURE

According to a first aspect of the present invention, it is proposed an urine analyzer device, configured to be installed in a toilet bowl, to be used several times, the device comprising:
- a holder member (9), to attach the device to the rim of the toilet bowl,
- an electronic unit (4), enclosed in a housing,
- a urine reception area (2), with at least one electro-chemical sensor (3), configured to measure a quantity of at least a substance, such as physiological compound or chemical component, contained in urine,
- a wireless coupler (5) to send resulting data to a remote computing device (50), wherein the electro-chemical sensor (3) comprises at least one ion selective Field Effect Transistor (ISFET), configured to sense levels of one or more physiological ions.

Thereby there is provided a urine analyzer device, readily available at home, simply installed in a toilet bowl, and that can be used several times subsequently.

Thanks to the disclosed features, an individual can follow some health indicators like pH of urine, or the concentration of one or more physiological ions in urine.

The measure of the quantity of one above-mentioned substance (like Na+, K+, Ca2+, Mg2+, Cl— . . . ) is advantageously made in situ, within the urine analyzer device; no additional device nearby the toilet is required.

Thanks to the coupling with a remote internet-enabled device, the user can share some of the collected data with a physician, hospital practitioner, etc. . . . .

The remote computing device can be a smartphone, but it should be understood that, instead of a smartphone, any more generally speaking portable electronic device can also be used (such as a tablet, a phablet, a PDA, a laptop computer, etc).

In various embodiments of the invention, one may possibly have recourse in addition to one and/or other of the following features/arrangements.

According to one option, the ion selective Field Effect Transistor comprises a reference electrode at the gate area of the transistor, the reference electrode containing a gel electrolyte, and a urine sample when present is interposed between the reference electrode and the gate port (G) of the transistor. This configuration named "wet configuration" is simple and reliable.

According to one option, the ion selective Field Effect Transistor comprises a reference electrode at the gate area of the transistor, the reference electrode containing powder or solid compound and a urine sample when present is interposed between the reference electrode and the gate port (G) of the transistor. This configuration named "dry configuration" is easy to prepare and store before use.

According to one option, the ion selective Field Effect Transistor is selective to hydrogen ions, whereby the pH of urine is measured with a sensitive membrane interposed between urine sample when present and the gate port (G) of the transistor; we note here that in order to maintain the pH of blood in a narrow range [7.35-7.45], pH in urine varies in the range [4.5-8].

The device may further comprise at least two additional ion selective Field Effect Transistors:
- one for measuring the concentration of Ca2+ ions to determine Calcium level in urine,
- one for measuring the concentration of K+ ions to determine the Potassium level in urine, each of them comprising a specific ion selective membrane interposed between a urine sample when present and the gate port (G) of the transistor.

Such a triple-sensor configuration turns to be a cost effective solution to follow three of the most important physiological ions.

According to one option, the device may further comprise a calibration solution reservoir arranged above the electro-chemical sensor to periodically provide a drop of calibration solution on the ion selective Field Effect Transistor, preferably one drop every period, said period being comprised between 15 and 45 days. Periodic recalibration enables to compensate for the drift.

When the device comprises two or more ion selective Field Effect Transistors, at least two ion selective Field Effect Transistors can advantageously share a same reference electrode (80). This further optimizes the cost of the solution.

According to one option, the reception area further comprises as electro chemical sensor at least an (biological) enzyme selective Field Effect Transistor (enFET). One or more membranes each selective to a particular compound enables to sense levels of some products like albumin, glucose, blood cells, nitrites, etc. . . . .

The enzyme selective Field Effect Transistor may comprise a reference electrode; this reference electrode may be preferably made from Ag/AgCl. This is easy to prepare and store before use.

The electro-chemical sensor (3) may further comprise a 3-electrode sensing unit (8"), provided with a reference electrode, a working electrode and a counter electrode, all arranged in a screen printed electrode configuration. Mechatronic integration can thus be optimized.

The urine reception area may comprise a porous structure that can be wetted by a flow of urine excreted by a user, and rinsed subsequently by the flush of the toilet. The measure can be performed nearly on-the-fly; since a small quantity (but sufficient) of urine is retained by the porous structure. The rinsing can be accompanied by a calibration/recalibration operation.

The urine reception area can form a cup, the device further comprising a controlled discharge valve.→buffer volume to ease optical sensing.

There may be provided a user feedback formed as a visual or auditive feedback.

This provides a Led light signal or a Beep to acknowledge: exemplified messages are "enough urine"/"end of measurement".

The electronic unit 4 may be at least partly housed in the holder member 9. This allows a good mechatronics integration. The device is small, easy to install; The device can be easily removed when cleaning the toilet bowl;

The urine reception area can be movable with respect to the holder member 9 such that the urine reception area can be located closer to the center of the bowl upon actuation from the user. This can be a mechanical linkage or a degree of freedom enabling to displace the urine reception area. Automatic return to a side position is preferred, e.g. when enough urine is received.

The electro chemical sensor may be configured to measure a quantity of one or more of the following substances: H+, Na+, K+, Ca2+, Mg2+, Cl—, $H_2O_2$, Glucose, Nitrites, Proteins, Oestrogenes, Luteinine Hormone, Beta-HCG Hormone (pregnancy marker), Creatinin.

Thereby, many health indicators can be followed. Particularly, albumin/protein levels present in urine can be measured and followed over time. Particularly, pregnancy testing can be provided with this device.

The urine analyser device may further comprise an optical sensor 6, configured to measure color and opacity of the urine; Thereby urine density and color index can be inferred as personal biological index(es) to be followed.

The urine reception area 2 is detachably mounted to the holder member. (for deep cleaning and/or exchange after N uses)

The device may further comprise a microphone and/or a basic fingerprint sensor arranged on the portion of the device located outside the toilet bowl. For User recognition among several users;

According to a second aspect of the present invention, it is proposed a system comprising a device according to claim 1 and a toilet seat 7 having weight sensing elements and impedance measurement elements, configured to recognise a particular user pattern among a plurality of users patterns, and to allocate results of urine analysis to the recognised particular user. This configuration is convenient for selective management of multiple users.

DETAILED DESCRIPTION OF THE DRAWINGS

Other features and advantages of the invention appear from the following detailed description of one of its embodiments, given by way of non-limiting example, and with reference to the accompanying drawings, in which.

DETAILED DESCRIPTION OF THE DISCLOSURE

In the figures, the same references denote identical or similar elements.

Figure 1:
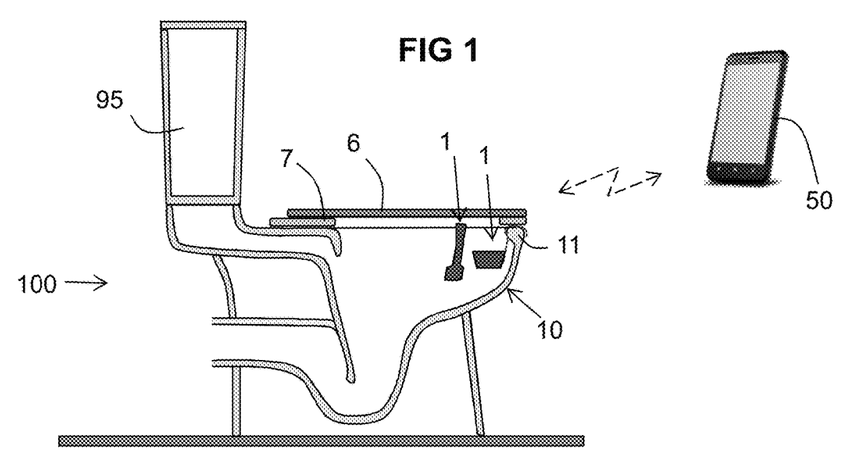
FIG. 1 shows a schematic sectional view of a toilet equipped with a urine analyzer device according to the present disclosure, with two possible embodiments.
Figure 2:
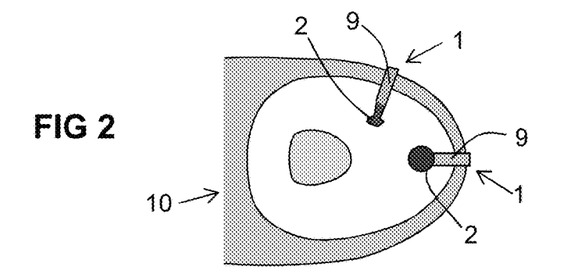
FIG. 2 shows a schematic top view of a toilet of FIG. 1.
Figure 3:
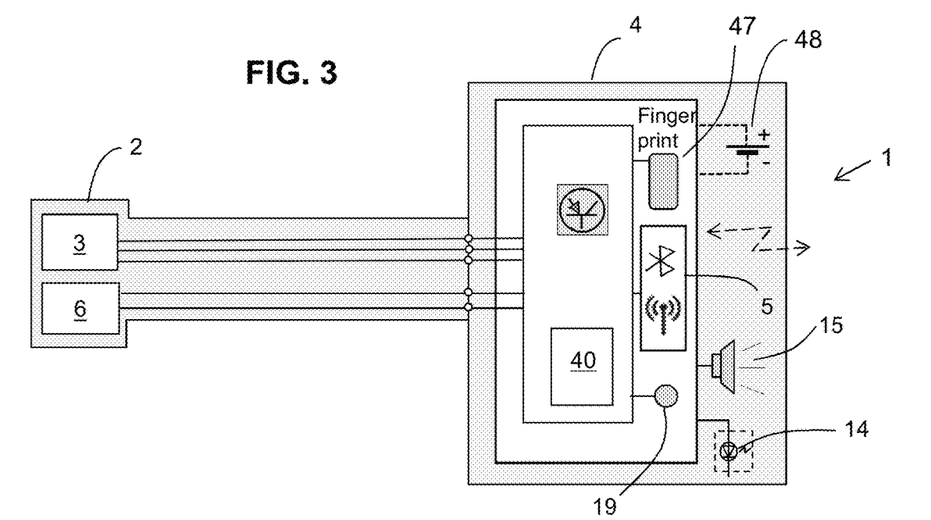
FIG. 3 shows a functional and structural block diagram

FIGS. 1 and 2 show a toilet 100 whose overall structure is known. Conventionally, the toilet comprises a water reservoir 95, a bowl 10, a toilet seat 7 and a toilet cover 6.

Further, there is provided a urine analyzer device 1. For the sake of explanation, there are shown two different devices in the illustration given in FIGS. 1 and 2, but of course the toilet can be equipped with only one urine analyzer device.

This urine analyzer device is removably attached to the rim 11 of the bowl. To this end, the urine analyzer device comprises a holder member 9, to attach the device to the rim of the toilet bowl. The holder member 9 exhibits a width comprised between 3 cm and 10 cm, and a small thickness to lodge between the upper border of the bowl rim 11 and the lower border of the seat 7, in other words the thickness is slightly smaller than the available gap G defined by the seat spacer pads 71. (see FIGS. 6A & 6B).

The urine analyzer device comprises a urine reception area 2, located inside the bowl.

There may be provided a possibility of movement of the reception area 2 with regard to the bowl body, toward the center of the bowl, which will be detailed later. The urine reception area 2 is arranged to be located, when it is at rest position in the peripheral flow of flushing water, for rinsing purpose and possibly recalibration purpose.

The urine analyzer device comprises an electronic unit 4, enclosed in a housing. The housing is preferably watertight. The urine analyzer device comprises a battery 48, a wireless coupler 5, such as Bluetooth wireless coupler, an indicator Led 14 and possibly an small loudspeaker or beeper/buzzer 15.

Additionally, there may be provided a microphone 19, a fingerprint pad 47 whose purpose will be given later.

According to one embodiment, there is provided a housing in a monolithic fashion, which includes, besides the electronic unit 4, also the battery and an extension member bearing the urine reception area 2.

According to another embodiment, the holder member 9 can be distinct from the housing including the electronic unit, the housing being attached in a fixed manner or in articulated manner to the holder member 9. The electronic unit 4 can be arranged with the holder member 9 in a single housing.

The device according the present invention is rather small, and its weight is less than 200 g, preferably less than 150 g.

The urine reception area 2 is permeable to water and/or urine.

The urine reception area 2 comprises at least a electro-chemical sensor 3. The electro-chemical electrode sensor 3 is configured to measure a quantity of at least one chemical substance, such as a physiological compound or other chemical component including ions, contained in urine.

The term "physiological compound" should be understood as any chemical species naturally contained in the human body, from the simplest ions to proteins and amino acids.

The term "chemical component" should be understood as some chemical species that are not naturally contained in the human body, like drugs, lead (Pb), mercury (Hg) and so on.

Among the substances which are targeted are the following:
  hydrogen ions (reflecting pH index)
  Sodium, Potassium, Calcium, Magnesium, Chloride,
  $H_2O_2$ (Hydrogen peroxide)
  Glucose/Proteins/Oestrogens/luteinine Hormone/Beta-HCG Hormone (pregnancy marker)/Creatinin/PSA Antigen (prostate disorder marker).

As some examples among others, here below are the range and sensitivity of electro-chemical sensor with regard to particular substances:

| | | |
|---|---|---|
| luteinine Hormone | from 0.2 mUI/ml to 80 mUI/ml | sensitivity: 0.2 mUI/ml |
| Creatinin | from 5 mg/ml to 20 mg/ml | sensitivity: 1 mg/ml |
| Albumin | from 75 µg/ml to 750 µg/ml | sensitivity: 30 µg/ml |

Among the physiological ions which are targeted are the following: H+, Na+, K+, Mg2+, Ca2+, Cl—.

Figure 4:
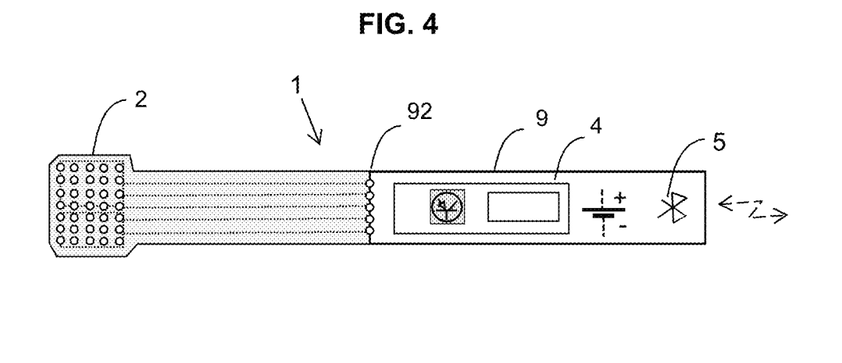
FIG. 4 shows a schematic layout and one example of configuration of the device
Figure 4A:
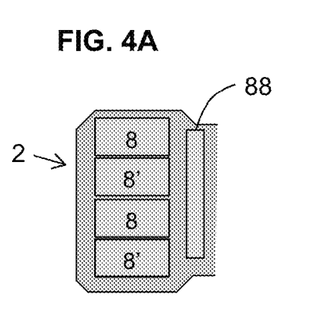
FIGS. 4A and 4B show enlarged views of variants of the reception area with several selective sensing devices.

There may be provided more than one electro-chemical sensor, each specialized in detecting a subset of the above-mentioned substances, as illustrated at FIG. 4A.

Figure 7:
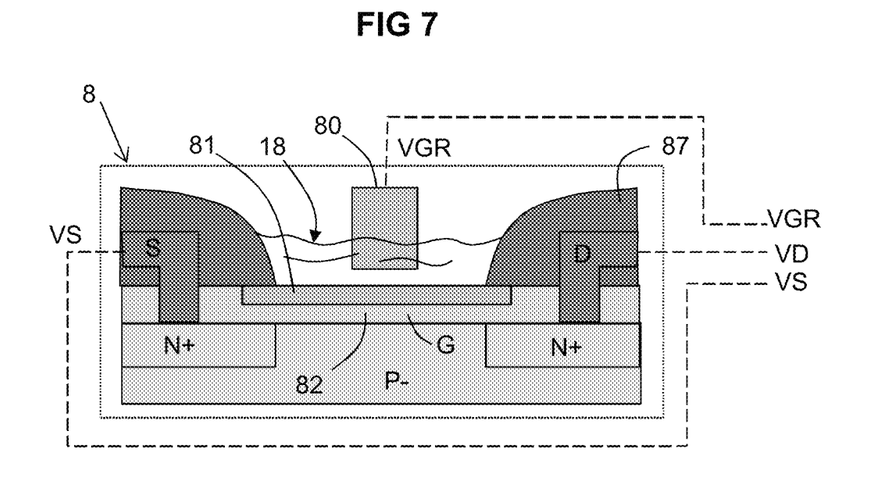
FIG. 7 illustrates diagrammatically a ISFET, i.e. a ion selective Field Effect Transistor.

One particular type of electro-chemical sensor proposed is a ion selective Field Effect Transistor (abbreviated in 'ISFET'), denoted 8 and illustrated on FIG. 7.

ISFET principle relies on a silicon chip which, when placed in contact with a test solution, urine sample in the present case, detects and measures the variable voltage potential between its surface and underlying semiconductor material. This variable potential is proportional to the ion concentration in the sample, and is used to determine the concentration of the ions of interest).

In the case of pH measurement, pH value is a function of H+ ion concentration. The ion sensitive membrane is formed by the semi-conductor itself (SiO2, Si3N4, Al2O3 or Ta2O5) and forms the gate port 82.

In the case of other ions (Na+, Mg2+, Ca2+, K+, Cl—), a highly selective organic membrane 81 specific to the respective ion of interest is arranged on top of the gate semiconductor 82, in other words the selective organic membrane 81 is interposed between the test solution (urine sample here) and the gate electrode.

Epoxy coating 87 isolates Drain and Source electrodes. As shown in FIG. 7, such epoxy coating forms a cup in which the urine sample 18 is held opposite the gate electrode without interfering with the rest of the silicon layers, notably the substrate. Substrate is doped P, whereas source and drain pads are doped N in the disclosed non limitative configuration.

ISFET also requires a reference electrode 80, which is placed at the gate area. The reference electrode 80 is held above the gate port of the transistor, and a urine sample when present is interposed between the reference electrode and the gate port (G) of the transistor.

In one embodiment, the reference electrode 80 contains a reference electrolyte solution placed in a small container having an exchange wall. In one particular embodiment, it can be a small container made of aluminum with the exchange wall being a ceramic foil.

The reference electrode 80 may be placed on the same chip as the rest of the transistor or externally. The reference electrode 80 is electrically coupled to a gate reference voltage denoted VGR.

The exchange of ions between the urine sample 18 and the electrolyte contained in the reference electrode creates a Gate trigger voltage at the gate port (G) of the transistor.

The reference electrode 80 may comprise a gel solution, or a gel composition. The solution contained therein is gradually consumed and/or gradually leaks out of reference electrode.

According to one particular option, the leakage rate can be slowed if the reference electrode remains immersed in flushing water a certain time.

Alternatively, the reference electrode 80 may comprise powder or solid compound.

Alternatively, the reference electrode 80 may be constituted by a metallic compound.

The concentration of ion of interest reflects in the voltage of the gate port 82 and the current flowing between the Drain and Source electrode reflects in turn in an amplified fashion the concentration of ion of interest. Current flow and/or [VD–VS] voltage is used by the electronic unit 4 to determine ion concentration.

pH Measurement pH value is an index reflecting concentration of H+ ions. The ion sensitive membrane is the semiconductor made as a top deposited layer of the transistor assembly connecting the drain and the source.

The gate electrode G portion of the transistor assembly is in direct contact with the test solution 18. After each use, water from flushing is advantageously used to rinse the gate area of the ISFET. The flushing water is also advantageously used to recalibrate the sensor in case of drift with time, provided that the pH of tap water is known.

Other Ions

According to one option, there is provided an additional ISFET selective to other chemical species:

Calcium (Ca2+). Calcium helps with muscle contractions, nerve signaling, blood clotting, cell division, and forming/maintaining bones and teeth.

Normal range of (Ca2+) concentration in urine is: [100-300] mg/day

A specific membrane selective to let the Ca2+ ions pass through is used.

Potassium (K+); it helps keeping blood pressure levels stable, regulating heart contractions, helping with muscle functions.

Normal range of (K+) concentration in urine is: [25-100] mEq/day

A specific membrane selective to let the K+ ions pass through is used.

Magnesium (Mg2+).

Normal range of (Mg2+) concentration is: [1.7-2.4] mg/day

Sodium (Na+)

Normal range of (Na+) concentration is: [100-260] mEq/day

Chloride (Cl—)

Normal range of (Cl—) concentration is: [80-250] mEq/day

Similarly specific membranes selective to let respectively Mg2+, Ca2+, K+, Na+, Cl— ions pass through are used.

Calibration and Recalibration

For each ISFET, the process of the periodic drop of calibration solution and subsequent recalibration can be used as explained before for H+ and flush water.

A calibration solution (tap water or a specific calibration solution) is brought into contact with the gate area and the measure is compared to an expected value, which allows to determine a deviation that is to be compensated for.

According to one option, the device may further comprise a calibration solution reservoir 88 arranged above the electrolyte sensor 3 to periodically provide a drop of calibration solution on the ion selective Field Effect Transistor. The drop of such calibration solution is used to recalibrate the electrochemical sensor. This calibration solution may be tap water or a specific solution.

A miniaturized control valve (not shown at the figures except schematically at FIG. 10B) is used to release the above-mentioned drop of calibration solution. Such drop can be programmed to occur every month. Generally speaking, the recalibration with the drop preferably occurs every period comprised in the range [15 days-45 days].

Figure 8:
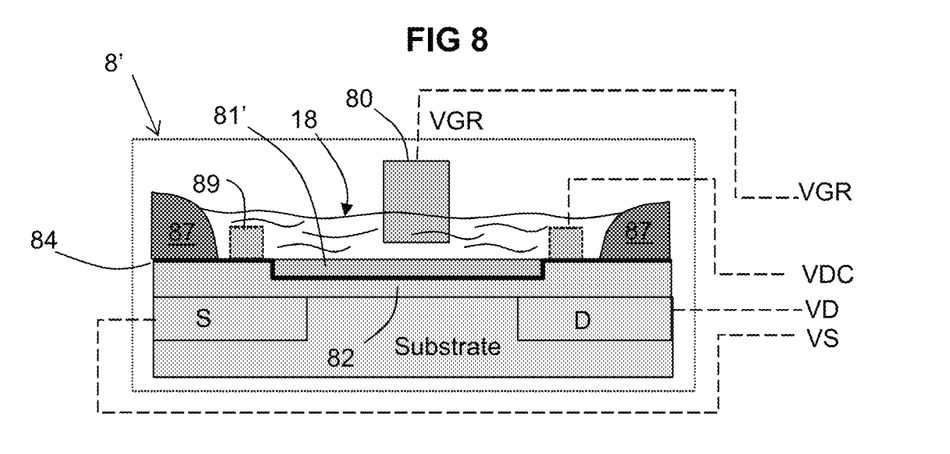
FIG. 8 illustrates diagrammatically an enFET, i.e. a enzyme selective Field Effect Transistor

Another particular type of electro-chemical sensor proposed is a biological selective Field Effect Transistor, otherwise called enzyme selective Field Effect Transistor (abbreviated in 'enFET'), denoted 8' and illustrated on FIG. 8.

The configuration is very similar what has been explained before regarding ISFET.

Filtering is here more elaborate and requires either an organic thin filtration membrane specifically configured to let some targeted molecules or a specific enzymatic membrane which reacts with the species of interest in the test sample. Reference 81' denotes the enzymatic layer which let the chemical species of interest go through, or reacts with the species of interest in the test sample.

The reference electrode 80 is electrically coupled to a gate reference voltage denoted VGR. The exchange of ions between the urine sample 18 and the reference electrode electrolyte creates a Gate trigger voltage at the gate port (G) of the transistor.

There may be provided optionally a surrounding counter electrode 89 which is set at a reference voltage VDC, which may be different from the reference voltage VGR of the reference electrode.

Epoxy coating 87 form a cup in which the urine sample 18 is held opposite the gate electrode without interfering with the rest of the silicon layers, notably the substrate. Here by contrast to the ISFET, the selective layer is more complicated to assemble; an intermediate foil denoted 84 is arranged on the silicon layers and the enzyme selective membrane 81' is arranged on top of the intermediate foil 84.

$H_2O_2$

The inventors have found that Urinary hydrogen peroxide ($H_2O_2$) is an amazingly good biomarker of oxidative stress, defined as the imbalance between Reactive Oxygen Species (ROS) production and antioxidant defense inside human organism. Oxidative stress is a risk factor playing a significant pathogenetic role for many diseases.

A specific membrane selective to let the $H_2O_2$ molecules pass through is used in a ISFET configuration.

Normal range of $H_2O_2$ in urine=15+/−9.8 μmol/L

Beta-HCG

Taking Beta-HCG Hormone (pregnancy marker) as another example, the enzymatic layer is designed to let only Beta-HCG Hormone pass across the membrane.

According to a particularly optimized configuration (not shown), there may be provided a reference electrode, a working electrode and a counter electrode, all arranged in a screen printed electrode configuration.

Generally speaking, there may be found several types FET sensor, either ISFET 8 or enFET 8' in the reception area 2, as illustrated in FIG. 4A, each one being selective to one ion type or one biological compound. Note that reference solution reservoir 88 may be either common to all the FET sensors, or there may be provided several individual reservoirs, or even a mix between the two solutions.

Figure 4B:
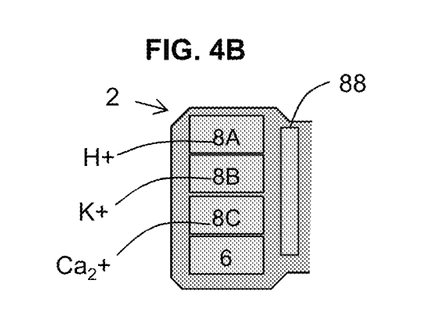

In a particular configuration, illustrated at FIG. 4B, there may be provided three ISFET devices, namely:

one (ref 8A) for measuring the concentration of H+ ions to determine pH, one (ref 8B) for measuring the concentration of K+ ions to determine the Potassium level, one (ref 8C) for measuring the concentration of Ca2+ ions to determine Calcium level, Of course additional ISFET for other ion species can be added to this configuration.

Figure 9:
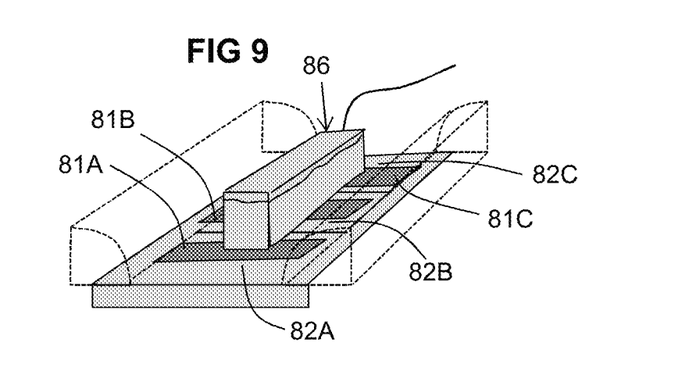
FIG. 9 illustrates diagrammatically a triple FET configuration, with a common shared reference electrode.

According to a particularly optimized configuration shown at FIG. 9, there may be provided 3 ion selective Field Effect Transistors, with a same reference electrode 86. A first ion selective Field Effect Transistor has a selective membrane 81A and a underlying gate 82A. A second ion selective Field Effect Transistor has a selective membrane 81B and a underlying gate 82B. A third ion selective Field Effect Transistor has a selective membrane 81C and a underlying gate 82C.

Apart from the electrolyte sensor, there may be provided an optical sensor 6. This optical sensor 6 is used to measure the opacity of the sampled urine, the color of the sampled urine and the concentration of the sampled urine. A light emitter directs light rays toward a urine sample contained in a cup 24; a photodiode receives the transmitted light power (may include a reflection on a mirror); one or several color filters can be interposed. Optical analysis is known and therefore not detailed here. Urine density and color index can be assessed by the electronic unit 4; personal biological ratings corresponding to Urine density and color index can thus be followed by the user. Content of the cup 24 may be purged by means of a miniaturized electro-valve.

Figure 6A:
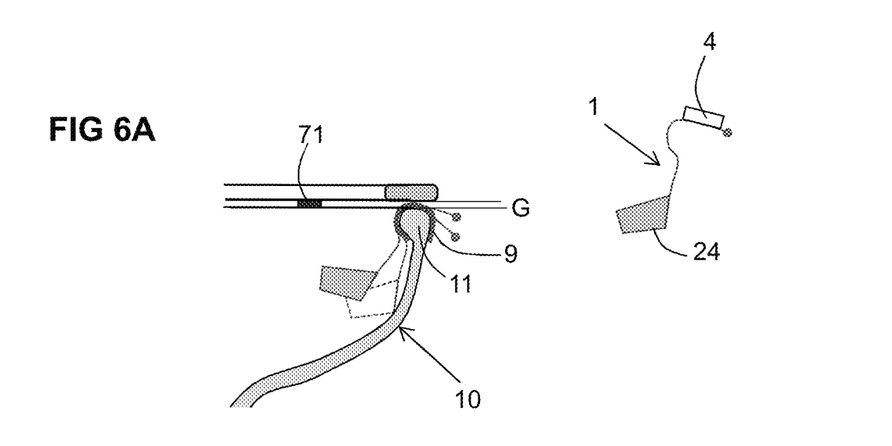
FIGS. 6A and 6B show a schematic layout of urine analyzer devices with collection position and rest position.

Regarding some mechanical aspects, the device can be monolithic as schematically shown at FIG. 6A.

According to one variant shown at FIG. 4, the device may be formed as two parts detachably associated to one another. A junction 92 with a connector joins the housing enclosing the electronic unit 4 and the reception area 2. The reception part can be removed for deep cleaning or completely exchanged by a new one.

Figure 6B:
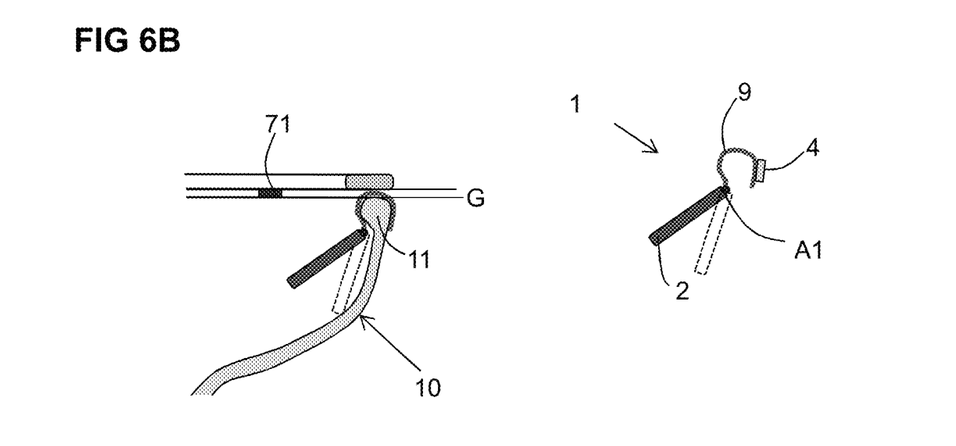

According to one option, there can be provided a degree of freedom between the holder member and the reception area, as illustrated at FIG. 6B. Axis Al denotes a possible rotation motion to move the sensitive area closer to the center of the bowl. This movement can be powered and controlled by the electronic unit 4.

However, at rest position, the urine reception area is preferably located adjacent to the internal wall of the bowl so it can receive at least partly some flushing water flow. There may be provided a deflector that helps directing the flushing flow toward the urine reception area in order to rinse the urine reception area. Additionally, There may be provided a purge valve that may be used to purge the content of the urine (or the water) retained inside the reception area; this also helps keeping the reference electrode 80 in a liquid to minimize leakage and extend its lifetime.

Alternatively the movement can be manually generated, with a handle to pull or a button to push and a linkage attached to a movable reception part.

The toilet in question may be used by several different users. Note that male and female hormones types and/or levels are always different; this allows to recognize if a male user or a female user is using the toilet.

Also interesting is a member of mictions per night/per day.

One way to recognize one user among several users is to place a weight sensor in the toilet seat 7. Additionally or alternatively, there may be provided contact electrodes to perform an impedance measurement; A particular signature is allocated to each user of the toilet, after initial teach-in proceedings. When the weight is used, a rather narrow range is allocated to each user.

Another way is to provide a fingerprint sensing device 47.

Another way is to provide a microphone with a basic voice recognition function such that a user of the toilet can just say a word (first name, or "it's me", or "hello") which is enough to distinguish one particular user among a defined group of users (e.g. a family).

Another way is to provide contact ECG electrodes and a ECG analyzer in the toilet seat, with one electrode in contact with one thigh and another configured to be touched by a finger.

Whenever a urine sampling is performed with no user recognition, the results is qualified as 'non affected' in the corresponding smartphone application.

Figure 5:
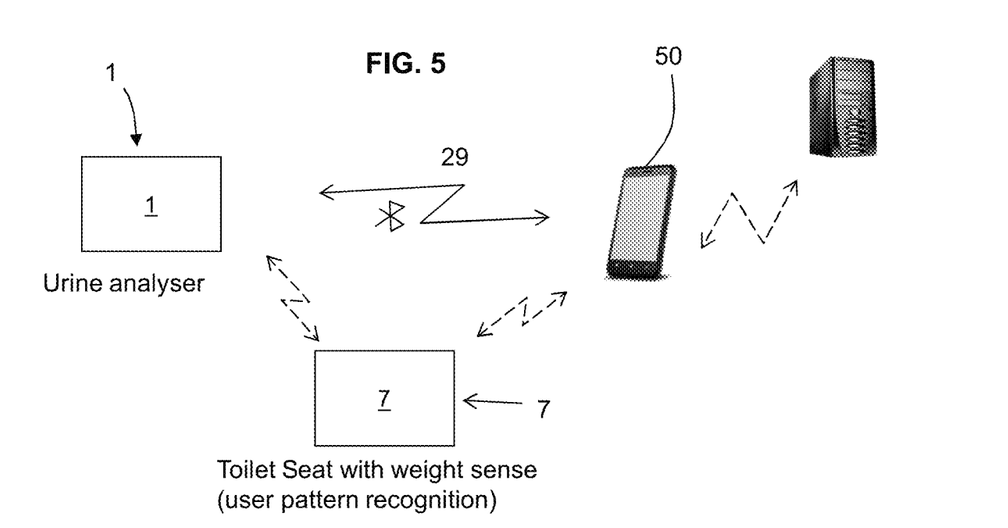
FIG. 5 shows an overall system view.

The system in which the urine analyzer device works includes a remote computing device 50. Any generally speaking "portable electronic device" can also be used, such as a smartphone, a tablet, a phablet, a PDA, a laptop computer, or any like wireless enabled device that can send and/or receive data through a wireless link 29. An application corresponding to the urine analyzer device is provided in one or more smartphone(s) if several users are involved.

For each user, a timechart with number of miction per day/night, evolution of pH and concentration of main chemical substance(s) can be displayed at the smartphone application.

The optional microphone 19 can be used to sense a flush sound signature. This provides automaticity of cleaning and recalibrating after toilet flush.

Regarding practical use, a female user has to direct the flow of urine toward the reception area, helped by the above mentioned displacement of the sensitive area; a male user, whether sitting or standing, has to direct the flow of urine toward the reception area.

Figure 10A:
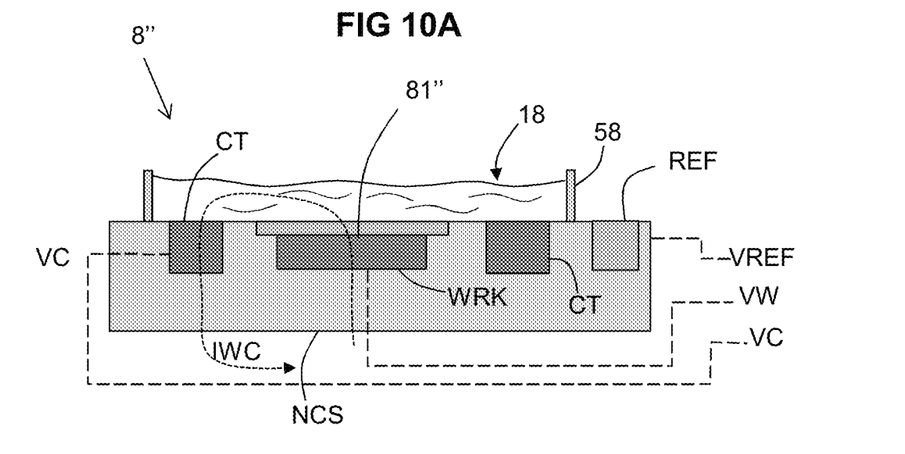
FIGS. 10A and A0B illustrate diagrammatically a 3-electrode configuration, respectively in elevation view and top view.
Figure 10B:
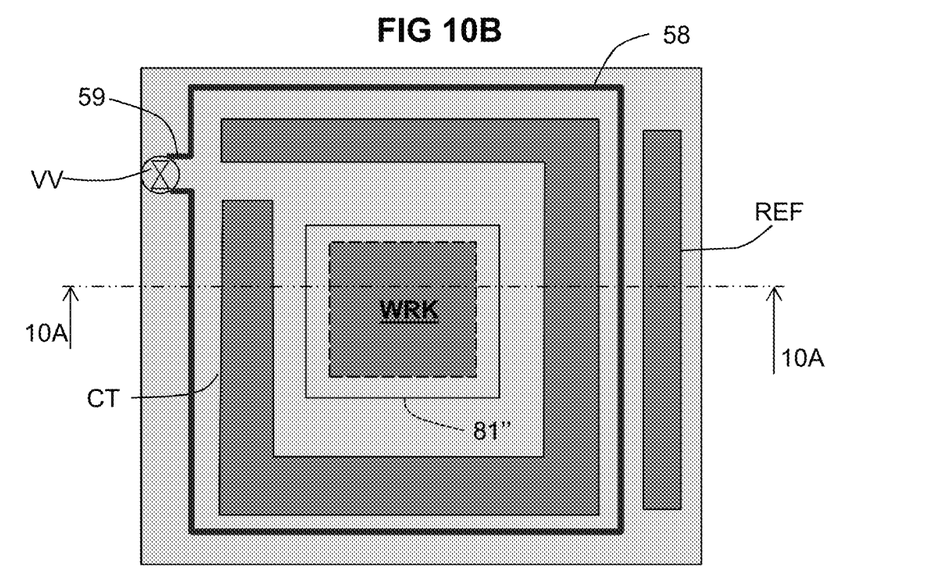

Another particular type of electro-chemical sensor proposed is a 3-electrode configuration, denoted 8" and illustrated on FIGS. 10A,10B. There are provided 3 electrodes on a non conductive substrate denoted NCS:

a reference electrode denoted REF (preferably kept at distance from the reaction site in order to maintain the substrate at a known and stable potential VREF), a working electrode denoted WRK through which a reactive current flow is sensed a counter electrode denoted CT which conducts the current flowing through the working electrode.

The working electrode serves as the transduction element in the biochemical reaction (also known as redox electrode); a selective or reactive membrane 81" (similar as explained above for enFET) is interposed between the urine test sample and the working electrode.

A urine sample 18 is held momentarily in a containing volume delimited by a border 58. At one location of the border there is provided a mouth 59 equipped with a controlled valve VV.

The current IWC flowing between the respective terminals VW,VC of working electrode and the counter electrode reflects the concentration of the species of interest.

The reference electrode is typically made from Ag/AgCl.

The working electrode is made of gold, carbon, diamond, platinum or any other metal not prone to corrosion.

According to one option, the working electrode is preferably a boron doped diamond electrode.

The invention claimed is:

1. A urine analyzer device configured to be placed in a standard toilet comprising a conventional toilet bowl and toilet seat, the urine analyzer device configured to be installed within the toilet bowl, the urine analyzer device being configured to be used several times subsequently, the device comprising:
   a watertight housing
   an extension member protruding from the watertight housing and bearing a urine reception area,
   battery enclosed in the watertight housing,
   an electronic unit, enclosed in the watertight housing,
   the urine reception area configured to measure a quantity of at least one substance contained in a urine sample, and at least one substance consisting of a physiological compound or chemical component, the urine reception area including at least one electro-chemical sensor, the electro-chemical sensor comprising at least a first transistor configured to sense levels of one or more physiological ions, the first transistor being an ion selective Field Effect Transistor,
   a wireless coupler to send resulting data to a remote computing device, and
   a calibration solution reservoir configured to be disposed inside the toilet bowl and overlapping the extension member, the calibration solution reservoir disposed adjacent to and above the ion selective Field Effect Transistor of the urine reception area, the calibration solution reservoir further configured to periodically provide a drop of calibration solution on a gate area of the ion selective Field Transistor.

2. The device of claim 1 wherein the ion selective Field Effect Transistor comprises a reference electrode at a gate area of the transistor, the reference electrode containing a gel reference electrolyte, and the urine sample when present is interposed between the reference electrode and a gate port of the transistor.

3. The device of claim 1 wherein the ion selective Field Effect Transistor comprises a reference electrode at a gate area of the transistor, the reference electrode containing powder or solid compound and the urine sample when present is interposed between the reference electrode and a gate port of the transistor.

4. The device of claim 1, wherein the ion selective Field Effect Transistor is selective to hydrogen ions, whereby the pH of the urine sample is measured, with a sensitive membrane interposed between the urine sample when present and a gate port of the transistor.

5. The device of claim 4, further comprising at least two additional ion selective Field Effect Transistors:
one for measuring a concentration of Ca2+ ions to determine Calcium level in the urine sample,
one for measuring a concentration of K+ ions to determine the Potassium level in the urine sample,
each of them comprising a specific ion selective membrane interposed between the urine sample when present and the gate port of the transistor.

6. The device of claim 1 where the device is configured to cause one drop of the calibration solution to be released every period, said period comprising between 15 and 45 days.

7. The device of claim 1, comprising two or more ion selective Field Effect Transistors, with at least two of the two or more ion selective Field Effect Transistors sharing a same reference electrode.

8. The device of claim 1 wherein the electro chemical sensor further comprises at least one enzyme selective Field Effect Transistor (enFET).

9. The device of claim 8 wherein the enzyme selective Field Effect Transistor comprises a reference electrode preferably made from Ag/AgCl compound.

10. The device of claim 1 wherein the electro-chemical sensor further comprises a 3-electrode sensing unit, provided with a reference electrode, a working electrode and a counter electrode, all arranged in a screen printed electrode configuration.

11. The device of claim 1 wherein the urine reception area comprises a porous structure that can be wetted by a flow of urine excreted by a user, and rinsed subsequently by a flush of the toilet.

12. The device of claim 1 wherein the urine reception area is a cup, the device further comprising a controlled discharge valve.

13. The device of claim 1 wherein there is provided a user feedback formed as a visual or audio feedback.

14. The device of claim 1 wherein the electronic unit is at least partly housed in the holder member.

15. The device of claim 1 wherein the urine reception area is movable with respect to the holder member such that the urine reception area can be located closer to the center of the bowl upon actuation from the user.

16. The device of claim 1, wherein the electro-chemical sensor is configured to measure a quantity of one or more of the following substances:
H+, Na+, K+, Ca2+, Mg2+, Cl—, H2O2, Glucose, Nitrites, Proteins, Oestrogenes, Luteinine Hormone, Beta-HCG Hormone, Creatinin.

17. The device of claim 1, further comprising an optical sensor, configured to measure color and opacity of the urine.

18. A system comprising a device according to claim 1 and a toilet seat having weight sensing elements and impedance measurement elements, configured to recognise a particular user pattern among a plurality of users' patterns, and to allocate results of urine analysis to the recognised particular user.

19. A system comprising a device according to claim 1 and a microphone and/or a basic fingerprint sensor located outside the toilet bowl.

20. The device of claim 1, further comprising a control valve to selectively release the calibration solution.

21. A urine analyzer device configured to be placed in a standard toilet comprising a conventional toilet bowl having a rim and a toilet seat, the urine analyzer device configured to be installed within the toilet bowl, the urine analyzer device being configured to be used several times subsequently, the device comprising:
a holder member configured to removably attach the device to the rim of the toilet bowl, the holder member further configured to squeeze the rim by extending from an outer portion of the rim to an inner portion of the rim in a vertical plane,
a watertight housing,
an extension member protruding from the watertight housing and bearing a urine reception area,
battery enclosed in the watertight housing,
an electronic unit, enclosed in the watertight housing,
the urine reception area configured to measure a quantity of at least one substance contained in a urine sample, at least one substance consisting of a physiological compound or chemical component, the urine reception area including at least one electro-chemical sensor configured to sense levels of one or more physiological ions, the electro-chemical sensor comprising at least a first transistor, the first transistor being an ion selective Field Effect Transistor,
a wireless coupler to send resulting data to a remote computing device, and
a calibration solution reservoir configured to be disposed inside the toilet bowl and overlapping the extension member, the calibration solution reservoir disposed adjacent to and above the ion selective Field Effect Transistor of the urine reception area, the calibration solution reservoir further configured to periodically provide a drop of calibration solution on a gate area of the ion selective Field Effect Transistor.

22. A urine analyzer device according to claim 21 wherein the holder member exhibits a width being less than 10 cm, and a thickness to lodge between an upper border of the rim and the lower border of the toilet seat, said thickness being smaller than the available gap defined by a spacer pad of the toilet seat.

* * * * *